United States Patent [19]

Vaillancourt

[11] Patent Number: 4,834,705
[45] Date of Patent: May 30, 1989

[54] DRUG DISPENSING SYSTEM

[76] Inventor: Vincent L. Vaillancourt, 30A Ridgedale Ave., East Hanover, N.J. 07981

[21] Appl. No.: 48,034

[22] Filed: May 11, 1987

[51] Int. Cl.⁴ ............... A61M 37/00; A61M 5/315
[52] U.S. Cl. .................................. 604/83; 604/236; 604/231
[58] Field of Search .............. 604/83, 85, 131, 150, 604/231, 236, 237, 90, 91, 191

[56]  References Cited

U.S. PATENT DOCUMENTS

| 657,440 | 9/1900 | McCaw | 604/236 |
|---|---|---|---|
| 1,563,627 | 12/1925 | Hein | 604/231 |
| 1,624,990 | 4/1927 | Smith | 604/236 |
| 3,699,961 | 10/1972 | Szpur | 604/237 |
| 3,976,068 | 8/1976 | Lundquist | 604/83 |
| 4,299,238 | 11/1981 | Baidwan et al. | 604/231 |
| 4,453,934 | 6/1984 | Gähwiler et al. | 604/191 |
| 4,464,174 | 8/1984 | Ennis | 604/236 |
| 4,690,154 | 9/1987 | Woodford et al. | 604/231 |

FOREIGN PATENT DOCUMENTS

| 117206 | 2/1901 | Fed. Rep. of Germany | 604/236 |
|---|---|---|---|
| 516790 | 1/1931 | Fed. Rep. of Germany | 604/236 |
| 2286657 | 4/1976 | France | 604/236 |

Primary Examiner—C. Fred Rosenbaum
Assistant Examiner—Kathleen A. Daley
Attorney, Agent, or Firm—Kenyon & Kenyon

[57]  ABSTRACT

The drug dispensing set includes a reservoir having a cylinder for receiving a primary infusion solution at the proximal end and a piston which slides within the cylinder in seal-tight relation. The piston includes a one-way valve to permit passage of the primary infusion solution to the distal side of the piston under pump pressure. A Y-site or three-way valve is connected in the tubing downstream of the reservoir to permit infusion of a drug dosage into the distal end of the cylinder while the piston moves towards the proximal end of the cylinder under the pressure of the delivered drug dosage. The drug dosage is subsequently dispensed from the reservoir when the pump is re-started and the primary infusion solution following the drug dosage serves to flush the tubing of the drug dosage.

16 Claims, 2 Drawing Sheets

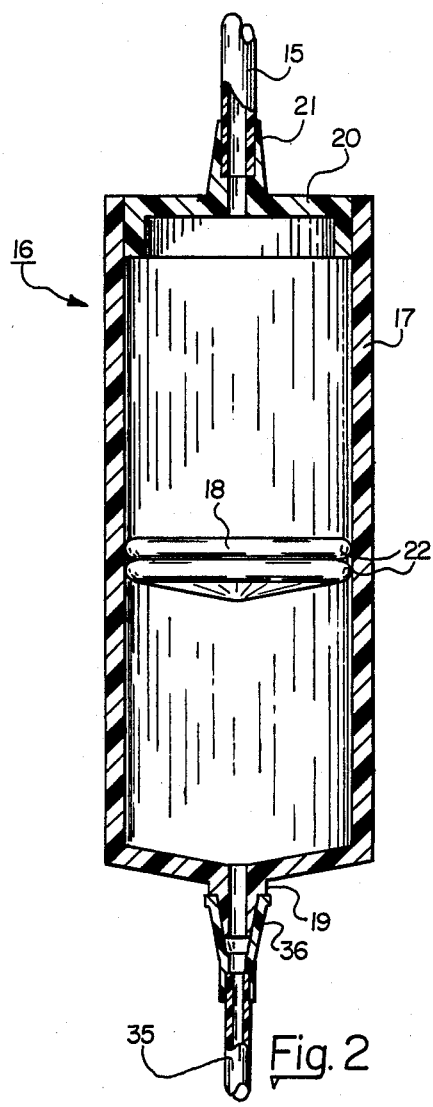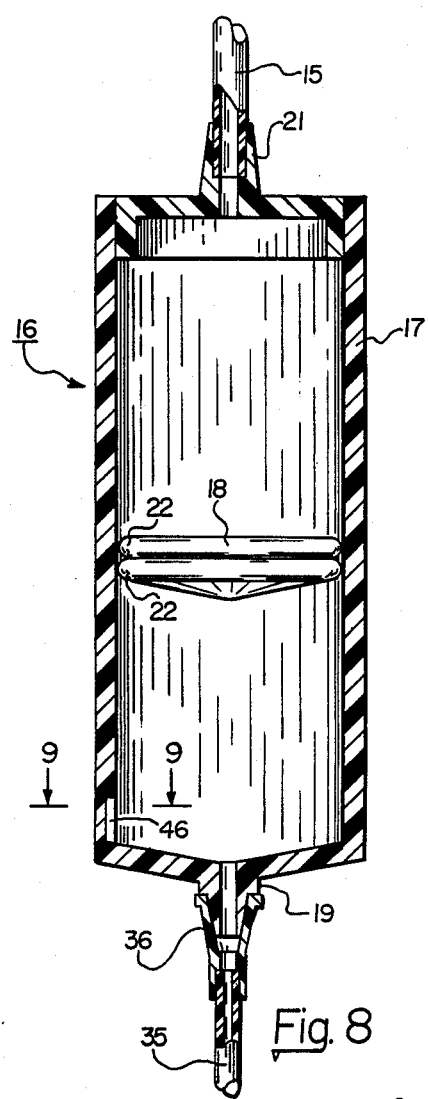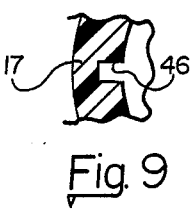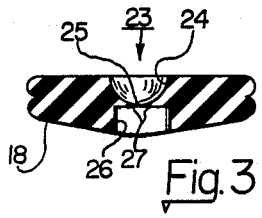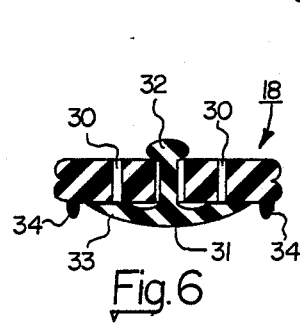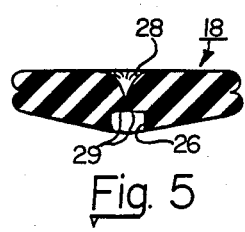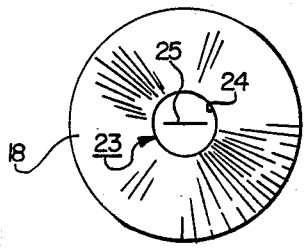

DRUG DISPENSING SYSTEM

This invention relates to a drug dispensing system. More particularly, this invention relates to an intravenous drug dispensing set.

Heretofore, various types of drug dispensing systems have been known for delivering drugs into a vascular system of a patient. In some cases, the drugs have been delivered via intravenous (IV) delivery sets. For example, it has been known to provide a dual-lumen delivery set wherein a primary infusion solution, such as a dextrose solution, is delivered through one lumen while a secondary drug solution is delivered through the other lumen. However, during use it has generally been necessary to provide a subsequent flush volume in the drug conveying lumen, i.e. the secondary infusion line, in order to clear the drug solution from the lumen. In addition, a priming volume must be determined for the delivery of the drug in appropriate quantities and over an appropriate length of time.

Other drug delivery sets have also been known which are of the single-lumen type. However, in these cases, a relatively complicated procedure must be followed in order to prime the lumen to convey the required drug dosage. Also, flush volumes of fluid must be used to clear the lumen of the drug dose after delivery of the drug to a patient.

Accordingly, it is an object of the invention to provide a relatively simple system for dispensing drug solutions to a patient.

It is another object of the invention to eliminate any need for flush solutions to clear a lumen through which a drug dosage has passed.

It is another object of the invention to be able to deliver accurate drug dosages to the vascular system of a patient.

It is another object of the invention to be able to deliver drug dosages intravenously to a patient in a simple manner.

Briefly, the invention provides a drug dispensing set which is comprised of a delivery tube for conveying a fluid such as an infusion fluid, a reservoir including a cylinder in communication with the delivery tube at a proximal end to receive the infusion fluid, a piston slidably mounted in seal-tight relation within the cylinder and means such as a one-way valve in the piston or a bypass duct in the cylinder to communicate a proximal side of the piston with a distal side of the piston for passage of the fluid to the distal side and a tubing communicating with the cylinder at a distal end to convey fluid therethrough. In addition, a means such as a Y-site or a three-way valve is provided in the tubing between the clamp and the reservoir for selective injection of a second fluid, such as a drug solution, into the tubing as well as a distal end of the cylinder. Where a Y-site is used, a clamp may be used to close the tubing to the passage of fluid.

During use, an infusion solution is conveyed from a suitable source through the delivery tube, for example under pressure by means of a pump, into the proximal end of the reservoir. At this time, the pressure of the solution causes the piston to bottom at the distal end of the cylinder. Thereafter, the one-way valve opens under the pressure of the fluid and passes the solution into the tubing, for example, for delivery to a needle implanted in the vascular system of the patient.

In the case of the Y-site embodiment, when a drug dosage is to be infused into the patient, the clamp is actuated to close the tubing to a continued flow of fluid to the patient, the pressure on the infusion solution is released and a drug delivering means, for example, a syringe is connected to the Y-site. Thereafter, the syringe delivers a drug solution into the tubing and into the distal end of the reservoir. This causes a "back-up" of the infusion solution in the tubing between the Y-site and the cylinder as well as movement of the piston towards the proximal end of the cylinder. Infusion of the drug solution eventually begins to fill the distal end of the reservoir with the drug solution while displacing the piston in the proximal direction.

In the embodiment employing a three-way valve in the tubing, the valve is simply actuated to deliver the drug solution into the tubing upstream of the valve.

The cylinder of the reservoir may be made of transparent material and may include a graduated scale which extends from the distal end towards the proximal end so as to permit a visual measurement of the drug dosage infused therein. In this respect, the scale may take into account the amount of dosage existing in the tubing extending from the cylinder to the three-way valve or this amount may be separately calculated.

During displacement of the piston towards the proximal end of the cylinder, the infusion solution is backed out of the cylinder into the delivery line. In this respect, a second three-way valve may be disposed within the delivery line in order to exhaust the infusion solution.

After a pre-determined dosage has been infused into the reservoir, the drug delivering means is disconnected and the reservoir is once again communicated with the needle via the tubing. The pressure is then re-exerted on the fluid in the reservoir so that the drug dosage can be delivered to the patient. In addition, after the piston "bottoms" in the cylinder, the infusion fluid follows so that there is no need for a separate flush solution to clear the tubing of the drug dosage.

These and other objects and advantages of the invention will become more apparent from the following detailed description taken in conjunction with the accompanying drawings wherein:

FIG. 2 illustrates an enlarged part cross-sectional view of a reservoir employed in the dispensing system in accordance with the invention;

FIG. 3 illustrates a cross-sectional view of a piston employed in the reservoir in accordance with the invention;

FIG. 4 illustrates a plan view of the piston of FIG. 3;

FIG. 5 illustrates a cross-sectional view of a modified piston having a one-way valve in accordance with the invention;

FIG. 6 illustrates a cross-sectional view a further modified piston having a one-way valve therein.

Figures 1, 7:
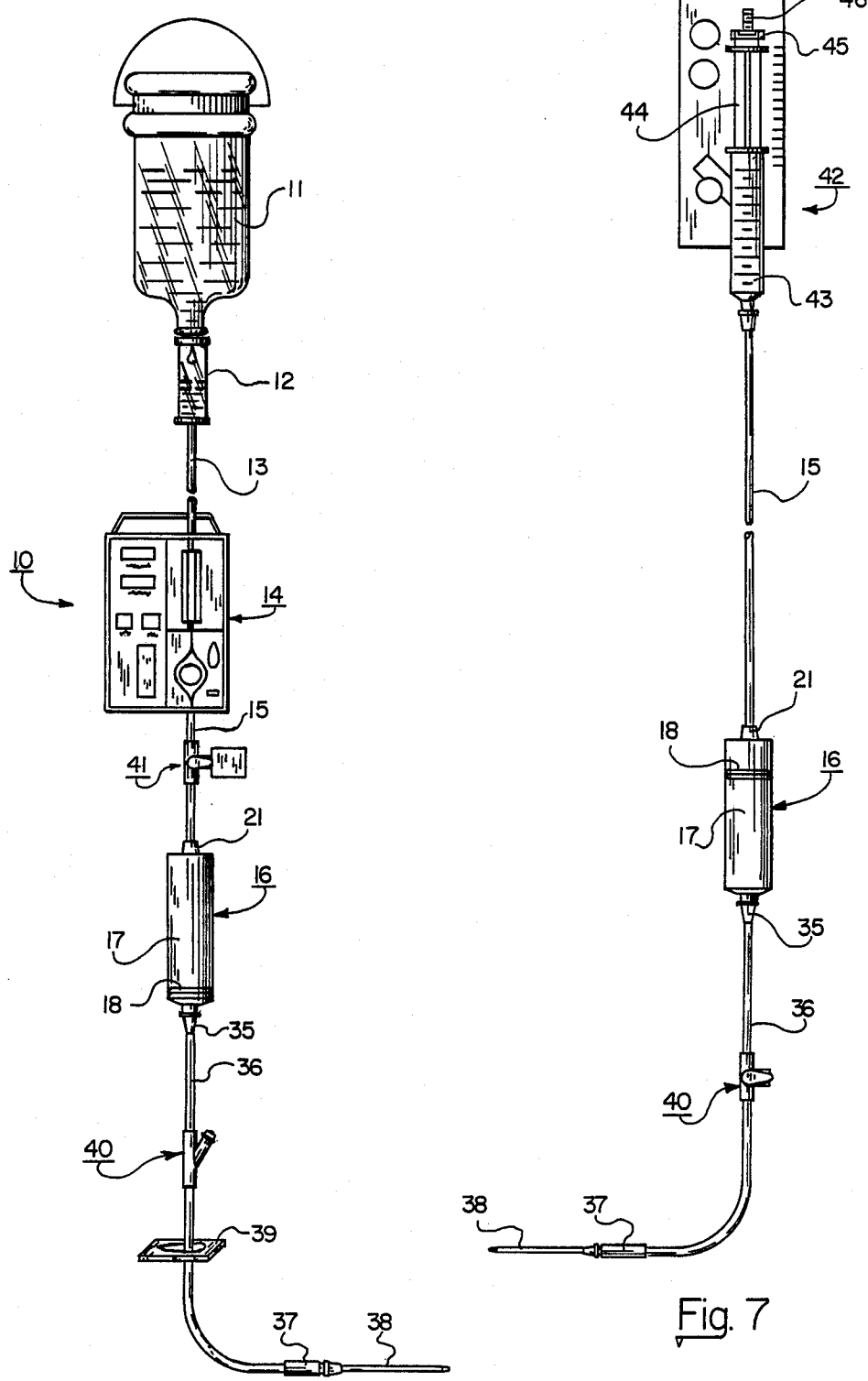
FIG. 1 illustrates a schematic view of a drug dispensing system constructed in accordance with the invention.
FIG. 7 illustrates a modified drug dispensing system in accordance with the invention.

Referring to FIG. 1, the drug dispensing system 10 includes a source of primary infusion solution, for example, an IV bottle 11 containing a dextrose solution, a drip chamber 12 as its known, a tube 13 to convey the primary infusion solution under gravity and a pump 14 for pumping the delivered primary infusion solution at a pre-determined pressure.

In addition, the dispensing system 10 includes a delivery tube 15 which extends from a delivery end of the pump 14 to a reservoir 16 for delivering the primary infusion solution under pressure.

Referring to FIGS. 1 and 2, the reservoir 16 includes a cylinder 17 which communicates with the delivery the 15 at a proximal end and a piston 18 which is slidably mounted in seal-tight relation within the cylinder 17. As indicated in FIG. 2, the cylinder 17 is closed at the lower end, as viewed, and includes a spigot 19 of reduced diameter for passage of a fluid therethrough. At the upper end, as viewed, the cylinder 17 is provided with an opening which is closed by a cover 20. The cover 20, in turn, has a spigot 21 which receives the delivery tube 15 for the conveyance of fluid therethrough. The cover 20 may be secured to the cylinder 17 in any suitable manner.

The cylinder 17 may be made of a transparent synthetic material and may be provided with a graduated scale which extends from the distal end towards the proximal end in order to provide a measurement of fluid within the cylinder 17.

Referring to FIGS. 2, 3 and 4, the piston 18 is of disc-shape and is provided with two annular shoulders 22 which sealingly engage the interior wall of the cylinder 17. In this respect, the piston 18 is free-floating so as to slide within the cylinder 17 under the pressure of the fluid therein. As indicated in FIGS. 3 and 4, a one-way valve 23 is provided in the piston 18 in order to communicate the proximal side of the piston 18 with the distal side of the piston 18 for passage of a fluid therethrough to the distal side. For example, where the piston 18 is made of an elastomer material such as rubber, the one-way valve constitutes a central recess 24 in the piston 18 and a slit 25 extending through the piston 18 to communicate the proximal side with the distal side.

As indicated in FIG. 3, the central portion of the piston 18 is shaped so that when the pressure in the recess 24 builds to a sufficient amount, relative to the pressure on the opposite side of the piston 18, the slit 25 enlarges so that fluid may pass through the slit 25. When the pressure decreases, the slit 25 closes due to the elastic nature of the material from which the piston 18 is made.

As indicated in FIG. 3, the recess 24 in the piston 18 has a hemispherical shape. In addition, a second recess 26 is provided on the opposite side of the piston 18 so that the two resulting thin-walled sections of the piston 18 form "flaps" 27 which define the boundary of the slit 25. As can be determined from FIG. 3, when the slit 25 is enlarged under the pressure of the fluid flow, the "flaps" 27 deflect downwardly, as viewed.

Alternatively, as shown in FIG. 5, wherein like reference characters indicate like parts as above, the one-way valve may be formed by a trumpet-shaped recess 28 in the piston 18'. In this case, the sections 29 of the piston defining the slit 25 tend to expand radially to provide for passage of the fluid under pressure.

Referring to FIG. 6, wherein like reference characters indicate like parts as above, the piston 18" has a one-way valve which includes a plurality of ports 30 which pass through the piston 18" and a valve body 31 having a stem 32 slidably mounted in the piston 18" and an enlarged head 33 which is disposed over the port 30. The arrangement of the valve body 31 is such that a pressurized flow from the proximal side to the distal side of the of the piston 18" causes the valve body 31 to move away from the ports 30 to "open" the valve.

However, when the pressure on the distal side of the 12 piston 18" is greater, the valve body 31 moves against the piston 18" to close off the ports 30.

As shown in FIG. 6, the stem 32 of the piston carries an enlarged end to prevent separation of the valve body 31 from the piston 18". In addition, the piston 18" may be provided with an annular shoulder 34 or a circumferential series of projections for spacing the valve body 31 from the bottom of the cylinder 17 when the piston 18" bottoms.

Referring to FIG. 1, the reservoir 16 is connected at the distal end with a tubing 35 via a suitable adaptor 36. The tubing 35, in turn, extends to a suitable means at the distal end for communicating with a vascular system of a patient. For example, the means may include a luer connection 37 and a needle 38, as is known.

In addition, a clamp 39 is provided about the tubing 35 in order to selectively close the tubing 35 to the passage of fluid there through. In addition, a means such as a Y-site 40 is provided in the tubing 35 between the clamp 39 and the reservoir 16 for the selective injection of a second fluid such as a drug dosage into the tubing 35 by suitable means such as a syringe (not shown).

A means such as a second three-way valve 41 may also be disposed in the delivery tube 15 between the pump 14 and the reservoir 16 for selectively delivering the primary infusion solution displaced from the reservoir 16 out of the system in response to delivery of the drug dosage into the reservoir 16 as described below. Alternatively, a one-way valve may be placed on the delivery tube 15 to exhaust a back-flow, for example, being actuated at a pressure of about 12 psi, into a suitable receptacle such as a bag (not shown). Such a receptacle may be removed from time-to-time after filling if necessary.

In use, the drug delivery system 10 can be set-up and connected to the vascular system of a patient in a conventional manner. At this time, the primary infusion solution from the IV bottle 11 is conveyed under gravity to the pump 14, which in turn, pumps the solution through the delivery tube 15 into the reservoir 16. Because the flow is under pressure, the piston 18 within the cylinder 17 moves to the distal end of the cylinder 17, as indicated in FIG. 1. Thereafter, the pressure of the solution causes opening of the one-way valve in the piston 18 so that the solution can be delivered through the tubing 35 into and through the needle 38. At this time, the valve 41 is set so as to convey the primary infusion solution to the patient.

When a secondary infusion solution such as a drug dosage is to be infused into the patient, the following steps are performed. First, the clamp 39 is actuated to close off the tubing 35 and the pump 14 is deactivated. Next, a suitable means such as a syringe is connected to the Y-site 40 so as to deliver a drug dose under pressure. At this time, the proximal end of the tubing 35 is disconnected from the distal end of the tubing 35 while being connected with the means delivering the drug dosage. Thus, the drug dosage first fills the distal end of the tubing 35 and thereafter begins to fill the reservoir cylinder 17. With the pressure of the dosage solution being greater than the pressure on the solution in the proximal end of the cylinder 17, the piston 18 begins to move toward the proximal end of the cylinder 17. During this time, the one-way valve in the piston 18 prevents passage of fluid from the distal side of the piston 18 to the proximal side of the piston 18. The solution which passes out of the cylinder 17 into the delivery line 15 may back up into and through the pump 14 or, may be exhausted from the system via the three-way valve 41.

After the drug dosage has filled the cylinder 17 to an appropriate level, the clamp 39 is opened to connect the proximal end of the tubing 35 with the distal end of the tubing 35. The valve 41 can then be re-set and the pump 14 restarted. At this time, any solution downstream of the valve 40 is infused into the patient. Immediately thereafter, the drug dosage begins to infuse into the patient. At the same time, the pump 14 delivers fresh primary infusion solution into the cylinder 17 under a pressure which is sufficient to cause the piston 18 to again move towards the distal end of the cylinder 17. During this time, the drug dosage is exhausted from the cylinder 17 into the tubing 35 leading to the patient. When the piston 18 bottoms in the cylinder 17, the one-way valve in the piston 18 opens so that the primary infusion solution is now passed into the tubing 35. At this time, the primary infusion solution not only serves as a source of pressure to infuse the drug dosage but also acts to flush the tubing 35 of the drug dosage.

Referring to FIG. 7, wherein like references characters indicate like parts above, the drug dispensing set may employ a syringe infusion pump 42 which is a conventional construction for delivering the primary infusion fluid directly into a delivery tube 15. The basic operation of this embodiment is similar to that described above and need not be further described.

As is known, the syringe pump 42 cooperates with a syringe housing 43 and a syringe plunger 44 slidably mounted in the syringe housing 43 to expel an infusion solution at predetermined pressures and rates. To this end, the pump 42 has a piston driver 45 at the top which abuts or holds the proximal end of the plunger 44 and a motorized worm shaft 46 which drives the driver 45 so as to advance the plunger 44 into the housing 43 at a controlled rate.

In order to permit the filling of the cylinder 17 of the reservoir 15 with a drug dosage, the driver 45 of the pump 42 is disengageable from the worm shaft, for example by means of an eccentric or clutch arrangement (not shown). The drug dosage can then be delivered into the reservoir 16 while the back-flow of primary infusion solution re-enters the syringe housing 43 causing the plunger 44 to retract. After filling of the reservoir 16, the driver 45 can be re-engaged with the worm shaft of the pump 42 and infusion of the drug dosage initiated.

The invention thus provides a drug dispensing set which can be easily connected to any suitable pump for the delivery of a primary infusion solution to a patient as well as a drug dispensing system which permits a relatively simple and accurate infusion of a drug dosage into a patient receiving a primary infusion solution.

The invention further provides a drug dispensing set which does not require flushing of the drug dosage tubing by independent means. In this respect, the drug dispensing system permits flushing of the drug dosage tubing by the primary infusion solution.

What is claimed is:

1. A drug dispensing set comprising
   a delivery tube for conveying a first fluid therethrough;
   a reservoir including a cylinder in communication with said tube at a proximal end to receive the first fluid, a free-floating piston slidably mounted in seal-tight relation within said cylinder and a one-way valve in said piston for communicating a proximal side of said piston with a distal side of said piston for passage of the first fluid therethrough to said distal side;
   as tubing communicating with said cylinder at a distal end to convey fluid therethrough; and
   second means in said tubing for selective injection of a second fluid into said tubing and a distal end of said cylinder.

2. A drug dispensing set as set forth in claim 1 wherein said cylinder is transparent and includes a graduated scale thereon extending from said distal end towards said proximal end.

3. A drug dispensing set as set forth in claim 1 wherein said piston is made of elastomer material and said one-way valve has a central recess in said piston and a slit in said piston to communicate a distal end of said recess with said distal side of said piston.

4. A drug dispensing set as set forth in claim 1 wherein said first means is a one-way valve including a plurality of ports passing through said piston and a valve body having a stem slidably mounted in said piston and an enlarged head disposed over said ports whereby a pressurized flow of the second fluid into said distal end of said cylinder biases said head against said piston to close said ports.

5. A drug dispensing set as forth in claim 1 which further comprises a three-way valve in said delivery tube for selectively delivering the first fluid to said reservoir and removing the first fluid displaced from said reservoir in response to delivery of a second fluid into said reservoir.

6. A drug dispensing set as set forth in claim 1 which further comprises a pump connected to said delivery tube for pumping the first fluid under pressure into said reservoir.

7. A drug dispensing set as set forth in claim 6 wherein said pump is a syringe infusion pump.

8. A drug dispensing set as set forth in claim 7 wherein said pump includes a syringe housing, a syringe plunger slidably mounted in said housing, a rotatable worm shaft and a flange connected to said plunger and releasably engaged with said shaft.

9. A drug dispensing system as set forth in claim 8 wherein said second means is a three-way valve.

10. A drug dispensing system as set forth in claim 8 wherein said second means is a Y-site and which further comprises a clamp downstream of said Y-site for closing said tubing to the passage of fluid therethrough.

11. A drug dispensing system comprising
    a delivery tube for conveying an infusion solution therethrough;
    a pump for pumping the infusion solution through said delivery tube under pressure;
    a reservoir including a cylinder connected at a proximal end to said tube to receive the infusion solution, a free-floating piston slidably mounted in seal tight relation with said cylinder a one-way valve in said piston for communicating a proximal side of said piston with a distal side of said piston for passage of a pressurized flow of the infusion solution form said proximal side to said distal side with said piston bottomed in said cylinder;
    a tubing connected to a distal side of said cylinder to convey the infusion solution therefrom; and
    second means in said tuning for selective injection of a drug dosage into said tubing and into a distal end of said cylinder during closing of said clamp in said tubing.

12. A drug dispensing system as set forth in claim 11 which further comprises a valve connected to said delivery tube for removing the infusion solution displaced from said cylinder in response to delivery of a drug dosage into said distal end of said cylinder.

13. A reservoir for a drug dispensing set comprising
a cylinder having a first port at a proximal end for conveying a first infusion fluid therethrough and a second port at a distal end for conveying fluid therethrough;
a free piston floating slidably mounted in seal-tight relation within said cylinder; and
a one-way valve in said piston to communicate a proximal side of said piston with a distal side of said piston for passage of a pressurized flow of the first fluid from said proximal side to said distal side.

14. A reservoir as set forth in claim 13 wherein said cylinder is transparent and includes a graduated scale thereon extending from said distal end towards said proximal end.

15. A reservoir as set forth in claim 13 wherein said piston is made of elastomer material and said one-way valve includes a central recess in said piston and a slit in said piston to communicate a distal end of said recess with said distal side of said piston.

16. A reservoir as set forth in claim 13, wherein said one-way valve includes a plurality of ports passing through said piston and a valve body having a stem slidably mounted in said piston and an enlarged head disposed over said parts whereby a pressurized flow of the second fluid into said distal end of said cylinder biases said head against said piston to close said ports.

* * * * *

UNITED STATES PATENT AND TRADEMARK OFFICE
CERTIFICATE OF CORRECTION

PATENT NO. : 4,834,705

DATED : May 30, 1989

INVENTOR(S) : VINCENT L. VAILLANCOURT

It is certified that error appears in the above-identified patent and that said Letters Patent is hereby corrected as shown below:

```
Column 2, line 58 "view a" should be -view of a -
Column 2, line 65 "its" should be -is-
Column 3, line 6 "the" (second occurrence) should be -tube-
Column 4, line 1 "12" should be deleted
Column 4, line 19 "there through" should be -therethrough-
Column 5, line 22 "references" should be -reference-
Column 5, line 23 "parts above" should be -parts as above-
Column 6, line 4 "as" should be -a-
Column 6, line 7 "and a" should be -and into a-
Column 6, line 19 "said first means is a one-way" should be -said
       one-way-
Column 6, line 19 "including" should be -includes-
Column 6, line 57 "with" should be -within-
Column 6, line 57 "a one-way" should be -and a one-way-
Column 6, line 61 "form" should be -from-
Column 7, line 11 "free piston" should be -free-floating piston-
```

Signed and Sealed this

Twenty-fourth Day of April, 1990

*Attest:*

HARRY F. MANBECK, JR.

*Attesting Officer*   *Commissioner of Patents and Trademarks*